United States Patent [19]

Schurter et al.

[11] Patent Number: 4,505,743

[45] Date of Patent: Mar. 19, 1985

[54] α-[4-(3-FLUORO-5'-HALOPYRIDYL-2'-OXY)-PHENOXY]-PROPIONIC ACID DERIVATIVES HAVING HERBICIDAL ACTIVITY

[75] Inventors: Rolf Schurter, Binningen; Hermann Rempfler, Ettingen, both of Switzerland

[73] Assignee: Ciba-Geigy Corporation, Ardsley, N.Y.

[21] Appl. No.: 450,815

[22] Filed: Dec. 20, 1982

[30] Foreign Application Priority Data

Dec. 31, 1981 [CH] Switzerland .......................... 8372/81

[51] Int. Cl.³ .................... C07D 213/64; A01N 43/40
[52] U.S. Cl. ....................................... 71/94; 546/300; 546/302
[58] Field of Search ...................... 546/302, 300; 71/94

[56] References Cited

U.S. PATENT DOCUMENTS

| | | | |
|---|---|---|---|
| 4,083,714 | 4/1978 | Takahashi et al. | 71/94 |
| 4,092,151 | 5/1978 | Takahashi et al. | 71/94 |
| 4,105,435 | 8/1978 | Nishiyama et al. | 71/94 |
| 4,133,675 | 1/1979 | Schurter et al. | 71/94 |
| 4,134,751 | 1/1979 | Nishiyama et al. | 71/94 |
| 4,140,520 | 2/1979 | Nishiyama et al. | 71/94 |
| 4,300,944 | 11/1981 | Bohner et al. | 71/94 |

FOREIGN PATENT DOCUMENTS

| | | | |
|---|---|---|---|
| 0000483 | 2/1979 | European Pat. Off. | 546/302 |
| 2002368 | 2/1979 | United Kingdom | 71/94 |

*Primary Examiner*—Alan L. Rotman
*Attorney, Agent, or Firm*—Frederick H. Rabin; Bruce M. Collins

[57] ABSTRACT

There are described novel α-[4-(3'-fluoro-5'-halopyridyl-2'-oxy)-phenoxy]-propionic acid esters and -thioesters having a herbicidal action and an action reducing the growth of grasses, which compounds correspond to the formula I

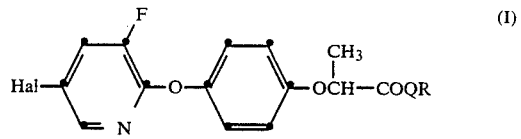

wherein
  Q is oxygen or sulfur,
  Hal is halogen, and
  R is hydrogen, a metal cation, an ammonium group, an unsubstituted or substituted alkyl, cycloalkyl, alkenyl or alkynyl group, or an imino ether group $-N=C\ R_1R_2$, in which $R_1$ and $R_2$ separately are each alkyl, or together they form a 4- or 5-membered methylene chain.

These compounds are suitable for selectively controlling weeds in crops of cultivated plants, or for reducing the growth of grasses.

4 Claims, No Drawings

α-[4-(3-FLUORO-5'-HALOPYRIDYL-2'-OXY)-PHENOXY]-PROPIONIC ACID DERIVATIVES HAVING HERBICIDAL ACTIVITY

The present invention relates to novel α-[4-(3'-fluoro-5'-halopyridyl-2'-oxy)-phenoxy]-propionic acid derivatives having herbicidal activity, to their production, to compositions containing these derivatives as active ingredients, and also to the use thereof as herbicides in general, and in particular for controlling weeds in crops of cultivated plants, such as cereals, rice, maize, soyabean and sugar beet.

The α-[4-(3'-fluoro-5'-halopyridyl-2'-oxy)-phenoxy]-propionic acid derivatives correspond to the formula I

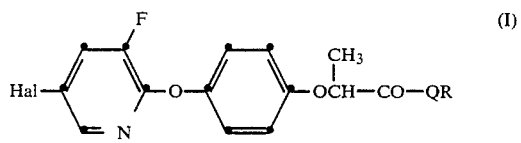

wherein
Hal is halogen
Q is oxygen or sulfur,
R is hydrogen, an alkali metal ion, or a quaternary $C_1$–$C_4$-alkylammonium group,
a $C_1$–$C_6$-alkyl group which is straight-chain or branched-chain, and which is unsubstituted or substituted by halogen, cyano, $C_1$–$C_4$-alkoxy, $C_1$–$C_4$-alkylcarbonyl, $C_1$–$C_4$-alkoxycarbonyl, carbamoyl or di-$C_1$–$C_4$-alkylcarbamoyl,
a $C_3$–$C_6$-cycloalkyl group,
a $C_3$–$C_6$-alkenyl group, which is straight-chain or branched-chain, and is unsubstituted or substituted by halogen,
a $C_3$–$C_6$-alkynyl group, which is straight-chain or branched-chain, and is unsubstituted or substituted by halogen,
a group

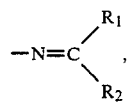

wherein
$R_1$ and $R_2$ separately are each a $C_1$–$C_4$-alkyl group, or together form a 4- or 5-membered methylene chain, which can be substituted by $C_1$–$C_4$-alkyl.

The most important representatives of the α-[4-(3'-fluoro-5'-halopyridyl-2'-oxy)-phenoxy]-propionic acid derivatives of the formula I according to the invention are those wherein
X is chlorine,
Q is oxygen, and
R is hydrogen or the ion of an alkali metal, $C_1$–$C_6$-alkyl which is straight-chain or branched-chain, or a group

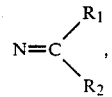

wherein
$R_1$ and $R_2$ separately are each $C_1$–$C_4$-alkyl.

Compounds which have proved particularly effective are:
α-[4-(4-chloro-2-fluoropyridyl-2-oxy)-phenoxy]-propionic acid methyl ester,
α-[4-(4-chloro-2-fluoropyridyl-2-oxy)-phenoxy]-propionic acid-n-propyl ester,
α-[4-(4-chloro-2-fluoropyridyl-2-oxy)-phenoxy]-propionic acid,
α-[4-(4-chloro-2-fluoropyridyl-2-oxy)-phenoxy]-propionic acid acetoxime ester.

The α-[4-(3'-fluoro-5'-halopyridyl-2'-oxy)-phenoxy]-propionic acid derivatives according to the invention are characterised by a good action against mono- and some dicotyledonous weeds; they are above all effective in the post-emergence process against undesirable weeds and wild grasses occurring in cultivated crops, such as crops of cereals, maize, rice, soyabean and sugar beet. A particularly valuable aspect is that it is possible with the novel derivatives to combat wild grasses which are very difficult to control, for example Avena fatua, Avena sterilis, Alopecurus myosuroides, Lolium perenne, Phalaris sp. Bromus tectorum and various species of Setaria and Panicum. The action under field conditions is achieved even with small applied amounts of less than 1 kg per hectare, at which levels the cultivated crops are not harmed, or are harmed to only a negligible extent Halopyridyloxy-α-phenoxy-propionic acid derivatives have been described in numerous publications (cp. for example the German Offenlegungsschriften Nos. 2,546,251, 2,649,706, 2,714,622 and 2,715,284, and the European Publications Nos. 483 and 1473). In these publications, the α-[4-(3'-fluoro-5'-halopyridyl-2'-oxy)-phenoxy]-propionic acid derivatives according to the present invention have in part been taken into consideration and concomitantly included in the scope. Compounds of this type have never however been produced or tested. They are distinguished from the known halopyridyloxy-α-phenoxy-propionic acids by a stronger action, and hence by the fact that it is possible to use them effectively in smaller amounts. Where the amount is sufficiently great however, there also occurs a total-herbicidal action. The novel compounds according to the present invention can be applied both in the pre-emergence process and in the post-emergence process. The amounts applied can vary within wide limits, for example between 0.05 and 5 kg of active substance per hectare.

Furthermore, the compounds of the formula I have favourable growth-regulating effects (growth inhibition). They inhibit in particular the growth of grasses.

α-[4-(3'-Fluoro-5'-halopyridyl-2'-oxy)-phenoxy]-propionic acid derivatives of the formula I which have proved very active are those wherein either
X is chlorine, bromine or iodine,
Q is hydrogen or sulfur,
R is hydrogen or the ion of an alkali metal, —$C_1$–$C_6$-alkyl, which is straight-chain or branched-chain and is substituted by halogen, hydroxyl, cyano, nitro, $C_1$–$C_4$-alkoxy-($C_1$–$C_4$-alkoxy)$_n$, $C_1$–$C_4$-alkylamino, di-($C_1$–$C_4$-alkylamino), $C_1$–$C_4$-alkoxycarbonyl, carbamoyl or di-($C_1$–$C_4$-alkyl)-carbamoyl, and
n is nought or a number from 1 to 5; or
X and Q have the above meanings, and R is a $C_2$–$C_6$-alkenyl or alkynyl group each of which is unsubstituted or substituted by halogen, hydroxyl or $C_1$–$C_4$-alkoxy;
and also those in which
X and Q have the above meanings, and
R is an imino ether group —N=C($R_3$)$_2$, in which $R_3$ separately are each $C_1$–$C_4$-alkyl, or together form a 4–5-membered polymethylene chain.

Particularly active is α-[4-(3'-fluoro-5'-chloropyridyl-2'-oxy)-phenoxy]-propionic acid, as well as the methyl and butyl esters thereof.

The novel compounds of the formula I are produced by methods known per se.

One of these processes comprises reacting a 2,5-dihalo-3-fluoropyridine of the formula II

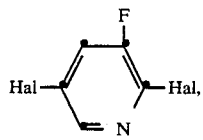
(II)

wherein Hal is halogen, in an inert solvent or diluent and in the presence of the equimolar amount of a base, with a 4-hydroxyphenoxy-α-propionic acid ester of the formula III,

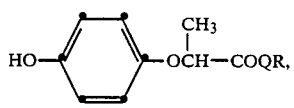
(III)

wherein Q and R have the meanings defined under the formul I.

A second process comprises reacting a 4-(3'-fluoro-5'-halopyridyl-2'-oxy)-phenol of the formula IV

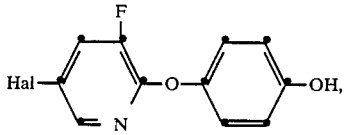
(IV)

wheren Hal is halogen, in an inert solvent or diluent and in the presence of the equimolar amount of a base, with an α-halopropionic acid ester of the formula V

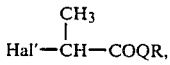
(V)

wherein Hal' is chlorine or bromine, and Q and R have the meanings defined under the formula I.

A further process comprises reacting an α-[4-(3'-fluoro-5'-halopyridyl-2'-oxy)-phenoxy]-propionic acid halide of the formula VI

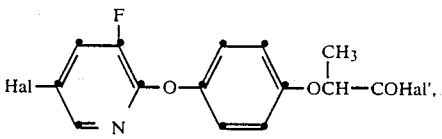
(VI)

wherein Hal' is chlorine or bromine, in an inert solvent or diluent and in the presence of the equimolar amount of a base, with an alcohol or thiol of the formula VII

HQR    (VII)

wherein Q and R have the meanings defined under the formula I.

In addition, the compounds of the formula I can be produced by reacting an α-[4-(3'-fluoro-5'-halopyridyl-2'-oxy)-phenoxy]-propionic acid or -thiopropionic acid of the formula IX

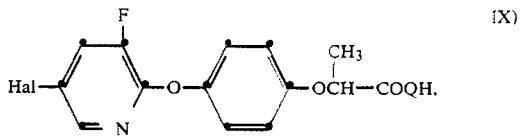
(IX)

wherein Hal and Q have the meanings defined under the formula I, in an inert solvent or diluent and in the presence of the equimolar amount of a base, with a halide of the formula X

Hal—R    (X)

wherein Hal is halogen, and R has the meaning defined under the formula I.

Finally, a further process comprises converting an α-[4-(3'-amino-5'-halopyridyl-2'-oxy)-phenoxy]-propionic acid ester of the formula XI

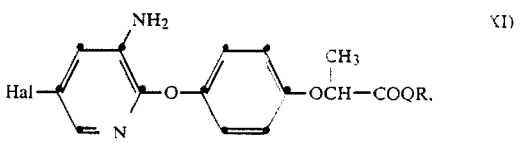
(XI)

wherein Hal, Q and R have the meanings defined under the formula I, using known methods, into a diazonium salt, and converting this further into the fluorine compounds.

A number of these reactions are advantageously carried out in an organic solvent or diluent inert to the reactants, for example an alcohol, ester, ether, ketone, dimethylformamide, dimethyl sulfoxide, acetonitrile or an aromatic compound, such as benzyl, toluene, and so forth.

The reaction temperatures are between −10° C. and 150° C., in practice however between room temperature and the boiling point of the solvent. Depending on the chosen starting material, the solvent and the temperature, the reaction time is between 1 hour up to about 1 day.

Where a halogen atom is detached in the reaction, the equimolar amount of an acid-binding agent should be used. Suitable as such is essentially any inorganic or organic base, for example NaOH, KOH, NaHCO$_3$, K$_2$CO$_3$ or K-tertbutylate, and amines, such as trimethylamine, triethylamine, pyridine, 4-dimethylaminopyridine, and so forth.

The novel active substances of the formula I are stable compounds which are soluble in customary organic solvents, such as alcohols, ethers, ketones, dimethylformamide, dimethyl sulfoxide, and the like. They are not explosive or corrosive, and the handling of them requires no special precautionary measures.

The compounds of the formula I are used either in an unmodified form or preferably together with auxiliaries customarily employed in formulation practice, and are thus processed in a known manner for example into the form of emulsion concentrates, directly sprayable or dilutable solutions, diluted emulsions, wettable powders, soluble powders, dusts or granulates, and also encapsulations in for example polymeric substances. The application processes, such as spraying, atomising, dusting, scattering or pouring, and likewise the type of composition, are selected to suit the objectives to be achieved and the given conditions.

The formulations, that is to say, the compositions or preparations containing the active substance of the formula I and optionally a solid or liquid additive, are produced in a known manner, for example by the intimate mixing and/or grinding of the active substances with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutyl- or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones such as cyclohexanone, strongly polar solvents, such as N-methyl-2-pyrrolidone, dimethyl sulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physicl properties, it is possible to add highly dispersed silicic acid or highly dispersed absorbent polymers. Suitable granulated adsorptive carriers are porous types, for example pumice, ground brick, sopiolite or bentonite; and suitable non-sorbent carriers are materials such as calcite or sand. There can also be used a great number of pre-granulated materials of inorganic or organic nature, such as in particular dolomite or ground plant residues.

Suitable surface-active compounds are, depending on the nature of the active substance of the formula I to be formulated, nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are for example the alkali metal, alkaline-earth metal or optionally substituted ammonium salts of higher fatty acids ($C_{10}$–$C_{20}$), for example the Na or K salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included among these are also the salts of sulfuric acid esters and sulfonic acids of fatty alcohol ethylene oxide adducts. The sulfonated benzimidazole derivatives preferably contain 2 sulfonic acid groups and a fatty acid group having 8–22 C atoms. Alkyarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenol-4-(4–14)-ethylene oxide adduct.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenolpolyethoxyethanols, castor oil polyglycol ethers, polypropylene/polyethyleneoxy adducts, tributylphenoxypolyethoxyethanol, polyethylene glycol and octylphenoxypolyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 carbon atoms and, as further substituents, lower, optionally halogenated alkyl, benzyl or lower hydroxyalkyl groups. The salts are preferably in the form of halides, methyl sulfates or ethyl sulphates, for example stearyl-trimethylammonium chloride or benzyldi(2-chloroethyl)ethylammonium bromide.

The tensides customarily used in formulation practice are described, inter alia, in the following publications:

"Mc Cutcheon's Detergents and Emulsifiers Annual," Mc Publishing Corp., Ringwood, N.J. 1979, Sisely and Wood, "Encyclopedia of Surface Active Agents," Chemical Publishing Co., Inc. New York, 1964.

These preparations contain as a rule 0.1 to 99%, particularly 0.1 to 95%, of active substance of the formula I, 1 to 99% of a solid or liquid additive, and 0 to 25%, especially 0.1 to 25%, of a tenside.

Whereas commercial products are preferably in the form of concentrated compositions, the compositions employed by the end-user are as a rule diluted.

The compositions can also contain further additives, such as stabilisers, antifoaming agent, viscosity regulators, binders and adhesives, and also fertilisers or other active ingredients for obtaining special effects.

The following Examples describe in detail the production of an α-[4-(3'-fluoro-5'-halopyridyl-2'-oxy)-phenoxy]-propionic acid ester of the formula I according to the invention, and also compositions containing such esters as active ingredients. Further esters according to the invention which are obtained analogously are listed in the Table following Example 1. Percentages relate to weight.

EXAMPLE 1

Production of
α-[4-(3'-fluoro-5'-chloropyridyl-2'-oxy)-phenoxy]-propionic acid methyl ester Compound No. 1

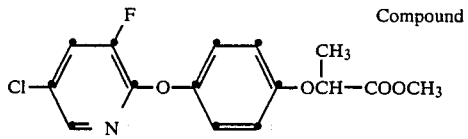

8.2 g (0.025 mol) of α-[4-(3'-amino-5'-chloropyridyl-2'-oxy)-phenoxy]-propionic acid methyl ester are dissolved in 120 ml of hydrofluoboric acid (HBF$_4$, 50%), and the solution is cooled to 0° C. There are then added dropwise 1.87 g (0.027 mol) of sodium nitrite in 20 ml of water during one hour. The product is filtered off after a further hour; it is then washed and (at room temperature and over phosphorus pentoxide) well dried. The diazonium-tetrafluoroborate thus obtained is heated at 150° C. for 10 minutes. The residue is dissolved still hot in methanol and, after the addition of an amount of active charcoal, it is filtered, and concentrated in a rotary evaporator. The yield after purification through a silica gel column (eluted with methylene chloride/hexane 6:1) is 5.5 g (67% of theory) of the title compound; m.p. 63°–64° C.

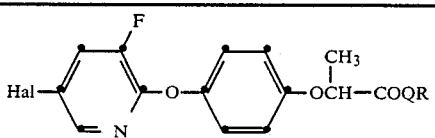

| No. | Hal | Q | R | Physical data |
|---|---|---|---|---|
| 1 | Cl | O | CH$_3$ | m.p. 63–64° C. |
| 2 | Br | O | CH$_3$ | |
| 3 | I | O | CH$_3$ | |
| 4 | Cl | O | C$_2$H$_5$ | |
| 5 | Br | S | C$_2$H$_5$ | |
| 6 | I | O | C$_2$H$_5$ | |
| 7 | Cl | O | (CH$_2$)$_2$CH$_3$ | oil |
| 8 | Br | O | (CH$_2$)$_2$CH$_3$ | |
| 9 | I | O | (CH$_2$)$_2$CH$_3$ | |
| 10 | Cl | O | CH(CH$_3$)$_2$ | |
| 11 | Cl | S | CH(CH$_3$)$_2$ | |
| 12 | Br | O | CH(CH$_3$)$_2$ | |
| 13 | I | O | CH(CH$_3$)$_2$ | |
| 14 | Cl | O | (CH$_2$)$_3$CH$_3$ | |
| 15 | Br | O | (CH$_2$)$_3$CH$_3$ | |
| 16 | I | O | (CH$_2$)$_3$CH$_3$ | |
| 17 | Cl | O | C$_2$H$_4$N(CH$_3$)$_2$ | |
| 18 | Cl | O | C$_2$H$_4$N(C$_2$H$_5$)$_2$ | |
| 19 | Cl | S | C$_2$H$_4$N(C$_2$H$_5$)$_2$ | |
| 20 | Cl | O | C$_3$H$_6$N(CH$_3$)$_2$ | |
| 21 | Br | O | C$_2$H$_4$N(C$_2$H$_5$)$_2$ | |
| 22 | I | O | C$_2$H$_4$N(C$_2$H$_5$)$_2$ | |
| 23 | Cl | O | C$_2$H$_4$N(C$_2$H$_4$OH)$_2$ | |
| 24 | Br | O | C$_2$H$_4$N(C$_2$H$_4$OH)$_2$ | |
| 25 | Cl | O | CH$_2$C≡CH | |
| 26 | Br | O | CH$_2$C≡CH | |
| 27 | I | O | CH$_2$C≡CH | |
| 28 | Cl | S | CH$_2$C≡CH | |
| 29 | Br | S | CH$_2$C≡CH | |
| 30 | I | S | CH$_2$C≡CH | |
| 31 | Cl | O | CH$_2$CH=CH$_2$ | |
| 32 | Br | O | CH$_2$CH=CH$_2$ | |
| 33 | I | O | CH$_2$CH=CH$_2$ | |
| 34 | Cl | S | CH$_2$CH=CH$_2$ | |
| 35 | Br | S | CH$_2$CH=CH$_2$ | |
| 36 | I | S | CH$_2$CH=CH$_2$ | |
| 37 | Cl | O | CH$_2$C(CH$_3$)=CH$_2$ | |
| 38 | Br | O | CH$_2$C(CH$_3$)=CH$_2$ | |

-continued

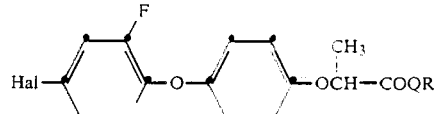

| No. | Hal | Q | R | Physical data |
|---|---|---|---|---|
| 39 | I | O | CH$_2$C(CH$_3$)=CH$_2$ | |
| 40 | Cl | S | CH$_2$C(CH$_3$)=CH$_2$ | |
| 41 | Br | S | CH$_2$C(CH$_3$)=CH$_2$ | |
| 42 | I | S | CH$_2$C(CH$_3$)=CH$_2$ | |
| 43 | Cl | O | CH$_2$CN | |
| 44 | Cl | S | CH$_2$CN | |
| 45 | Cl | O | CH(CH$_3$)CN | |
| 46 | Cl | O | N=C(CH$_3$)$_2$ | oil |
| 47 | Br | O | N=C(CH$_3$)$_2$ | |
| 48 | I | O | N=C(CH$_3$)$_2$ | |
| 49 | Cl | O | N=C(C$_2$H$_5$)$_2$ | |
| 50 | Br | O | N=C(C$_2$H$_5$)$_2$ | |
| 51 | I | O | N=C(C$_2$H$_5$)$_2$ | |
| 52 | Cl | O | N=C(CH$_3$)C$_2$H$_5$ | |
| 53 | Br | O | N=C(CH$_3$)C$_2$H$_5$ | |
| 54 | I | O | N=C(CH$_3$)C$_2$H$_5$ | |
| 55 | Cl | O | CH$_2$—C≡C—CH$_2$Cl | |
| 56 | Cl | O | CH$_2$—C(Br)=CH$_2$ | |
| 57 | Cl | O | CH$_2$—CH=CH—Cl | |
| 58 | Cl | O | C(CH$_3$)$_2$CN | |
| 59 | Br | S | CH$_2$—CH=CH—CH$_3$ | |
| 60 | Br | S | CH$_2$CH$_2$—CH=CH$_2$ | |
| 61 | Cl | O | 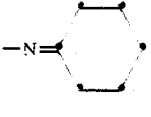 | |
| 62 | Br | O | (same pyridyl group) | |
| 63 | I | O | (same pyridyl group) | |
| 64 | Cl | O | CH$_2$COOCH$_3$ | |
| 65 | Cl | S | CH$_2$COOCH$_3$ | |
| 66 | Br | O | CH$_2$COOCH$_3$ | |
| 67 | Br | S | CH$_2$COOCH$_3$ | |
| 68 | I | O | CH$_2$COOCH$_3$ | |
| 69 | I | S | CH$_2$COOCH$_3$ | |
| 70 | Cl | O | CH(CH$_3$)COOC$_2$H$_5$ | |
| 71 | Cl | S | CH(CH$_3$)COOC$_2$H$_5$ | |
| 72 | Br | O | CH(CH$_3$)COOC$_2$H$_5$ | |
| 73 | Br | S | CH(CH$_3$)COOC$_2$H$_5$ | |
| 74 | I | O | CH(CH$_3$)COOC$_2$H$_5$ | |
| 75 | I | S | CH(CH$_3$)COOC$_2$H$_5$ | |
| 76 | Cl | O | CH$_2$CONH$_2$ | |
| 77 | Cl | O | CH$_2$CH$_2$COOCH$_3$ | |
| 78 | Cl | O | CH$_2$COOC$_4$H$_9$n | |
| 79 | I | O | CH$_2$COOC$_4$H$_9$n | |
| 80 | Cl | S | CH$_2$COOC$_4$H$_9$n | |
| 81 | Br | S | CH$_2$COOCH(CH$_3$)$_2$ | |
| 82 | Cl | S | CH$_2$CON(CH$_3$)$_2$ | |
| 83 | Cl | O | H | m.p. 95–97° C. |
| 84 | Br | O | H | |
| 85 | I | O | H | |
| 86 | Cl | O | Na | |
| 87 | Br | O | Na | |
| 88 | I | O | Na | |

EXAMPLE 2

Production of a formulation with liquid active ingredients of the formula I (%=percent by weight)

| Emulsion concentrates | a | b | c |
|---|---|---|---|
| α-[4-(3'-fluoro-5'-halopyridyl-2'-oxy)-phenoxy]-propionic acid methyl ester | 20% | 40% | 50% |
| calcium dodecylbenzenesulfonate | 5% | 8% | 5.8% |
| castor oil-polyethylene glycol ether (36 mols of ethylene oxide) | 5% | — | — |
| tributylphenol-polyethylene glycol ether (30 mols of ethylene oxide) | — | 12% | 4.2% |
| cyclohexanone | — | 15% | 20% |
| xylene mixture | 70% | 25% | 20% |

Emulsions of any required concentration can be produced from concentrates of this type by dilution with water.

| Solutions | a | b | c | d |
|---|---|---|---|---|
| active ingredient according to the formula I | 80% | 10% | 5% | 95% |
| ethylene glycol-monomethyl ether | 20% | — | — | — |
| polyethylene glycol MG 400 | — | 70% | — | — |
| N—methyl-2-pyrrolidone | — | 20% | — | — |
| epoxidised coconut oil | — | — | 1% | 5% |
| ligroin (boiling limites 160–190° C.) | — | — | 94% | — |

The solutions are suitable for application in the form of very fine drops.

| Granulates | a | b |
|---|---|---|
| active ingredient according to the formula I | 5% | 10% |
| kaolin | 94% | — |
| highly dispersed silicic acid | 1% | — |
| attapulgite | — | 90% |

The active ingredient is dissolved in methylene chloride; the solution is subsequently sprayed onto the carrier, and the solvent is evaporated off in vacuo.

| Dusts | a | b |
|---|---|---|
| active ingredient according to the formula I | 2% | 5% |
| highly dispersed silicic acid | 1% | 5% |
| talcum | 97% | — |
| kaolin | — | 90% |

Ready-for-use dusts are obtained by the intimate mixing together of the carriers with the active ingredient.

Formulation Examples for solid active ingredients of the formula I (%=percent by weight)

| Wettable powders | a | b |
|---|---|---|
| active ingredient of the formula I | 20% | 60% |
| sodium lignin sulfonate | 5% | 5% |
| sodium lauryl sulfate | 3% | — |
| sodium diisobutylnaphthalene sulfonate | — | 6% |
| octylphenolpolyethylene glycol ether (7–8 mols of ethylene oxide) | — | 2% |
| highly dispersed silicic acid | 5% | 27% |
| kaolin | 67% | — |

The active ingredient is well mixed with the additives and the mixture is thoroughly ground in a suitable mill. Wettable powders which can be diluted with water to give suspensions of the required concentration are obtained.

| Emulsion concentrate | |
|---|---|
| active ingredient of the formula I | 10% |
| octylphenol polyethylene glycol ether (4–5 mols of ethylene oxide) | 3% |
| calcium dodecylbenzenesulfonate | 3% |
| castor oil polyglycol ether (36 mols of ethylene oxide) | 4% |
| cyclohexanone | 30% |
| xylene mixture | 50% |

Emulsions of the required concentration can be obtained from this concentrate by dilution with water.

| Dusts | a | b |
|---|---|---|
| active ingredient of the formula I | 5% | 8% |
| talcum | 95% | — |
| kaolin | — | 92% |

Dusts ready for use are obtained by mixing the active substance with the carriers and grinding the mixture in a suitable mill.

| Extruder granulate | |
|---|---|
| active ingredient of the formula I | 10% |
| sodium lignin sulfonate | 2% |
| carboxymethylcellulose | 1% |
| kaolin | 87% |

The active ingredient is mixed and ground with the additives, and the mixture is moistened with water. This mixture is extruded and then dried in a stream of air.

| Coated granulate | |
|---|---|
| active ingredient of the formula I | 3% |
| polyethylene glycol (MG 200) | 3% |
| kaolin | 94% |

The finely ground active ingredient is evenly applied, in a mixer, to the kaolin moistened with polyethylene glycol. Dustfree coated granulates are obtained in this manner.

| Suspension concentrate | |
|---|---|
| active ingredient of the formula I | 40% |
| ethylene glycol | 10% |
| nonylphenolpolyethylene glycol ether (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the additives. There is thus obtained a suspension concentrate from which can be produced, by dilution with water, suspensions of the concentration required.

EXAMPLE 4

Testing of the herbicidal action

Pre-emergence herbicidal action (inhibition of germination)

Immediately after sowing of the test plants in pots in a greenhouse, the surface of the soil is sprayed with an aqueous dispersion of the active ingredient, which has been prepared either from a 25% emulsion concentrate, or from a 25% wettable powder in the case of active ingredients which cannot be prepared as emulsion concentrates owing to inadequate solubility. Varying concentrations are used, and the amount of active ingredient is calculated on the basis of kg per hectare. The pots are then kept in a greenhouse at 22°-25° C. with 50-70% relative humidity, and are regularly watered. The test results are evaluated after three weeks.

The condition of the plants is assessed according to the following scale of ratings:
9 plant has flourished as in the case of the untreated control plant,
6-8 slight damage, plant can recover,
4-5 medium damage, stunted growth,
2-3 severe damage,
1 plant has died or has not germinated.

The results are summarised below:

| plant | Compound 1 | | | 7 | | | 46 | | | 83 | | | A | | | B | | |
|---|---|---|---|---|---|---|---|---|---|---|---|---|---|---|---|---|---|---|
| | \multicolumn{15}{l}{Applied amount kg/hectare} | | | |
| | 1 | ½ | ¼ | 1 | ½ | ¼ | 1 | ½ | ¼ | 1 | ½ | ¼ | 1 | ½ | ¼ | 1 | ½ | ¼ |
| wheat | 2 6 7 | | | 4 6 8 | | | 4 6 8 | | | 4 6 8 | | | 8 9 9 | | | 9 9 9 | | |
| soyabean | 9 9 9 | | | 8 9 9 | | | 9 9 9 | | | 8 8 8 | | | 7 9 9 | | | 9 9 9 | | |
| cotton | 9 9 9 | | | 9 9 9 | | | 9 9 9 | | | 8 9 9 | | | 9 9 9 | | | 9 9 9 | | |
| sugar beet | 9 9 9 | | | 7 8 8 | | | 9 9 9 | | | 8 9 9 | | | 9 9 9 | | | 9 9 9 | | |
| Avena fatua | 1 2 2 | | | 2 2 3 | | | 2 3 3 | | | 3 3 3 | | | 6 9 9 | | | 9 9 9 | | |
| Bromus tectorum | 1 1 1 | | | 2 3 3 | | | 2 3 3 | | | 3 3 3 | | | 4 8 9 | | | 6 9 9 | | |
| Alopecurus myos. | 1 1 1 | | | 1 1 2 | | | 1 2 2 | | | 2 2 2 | | | 3 9 9 | | | 6 9 9 | | |
| Digitaria sang. | 1 1 1 | | | 1 1 2 | | | 1 1 2 | | | 1 1 2 | | | 2 2 6 | | | 2 2 7 | | |
| Echinochloa c.g. | 1 1 1 | | | 1 1 2 | | | 1 1 3 | | | 1 1 1 | | | 2 6 9 | | | 3 7 7 | | |
| Sorghum halepense | 1 1 1 | | | 1 2 3 | | | 2 3 3 | | | 1 2 2 | | | 4 7 9 | | | — — — | | |
| Rottboellia exaltata | 1 1 2 | | | 1 1 2 | | | 2 3 3 | | | 2 2 3 | | | 2 4 9 | | | 7 9 9 | | |

The compound
A is α-[4-(3,5-dichloropyridyl-2-oxy)-phenoxy]-propionic acid methyl ester, and
B is α-[4-(3,5-dichloropyridyl-2-oxy)-phenoxy]-propionic acid,
which are known from the German Offenlegungsschrift No. 2,546,251 (U.S. Pat. No. 3,046,553).

Post-emergence herbicidal action (contact herbicide)

A considerable number of weeds and cultivated plants, both monocotyledonous and dicotyledonous, are grown in pots in a greenhouse, and after emergence (in the 4- to 6-leaf stage) the plants are sprayed with an aqueous active-ingredient dispersion in varying dosages, expressed in kg of active ingredient per hectare, and the treated plants are kept at 24°-26° C. with 45-60% relative humidity. The test results are evaluated two weeks after the treatment. The results are summarised below:

| plant | Compound 1 | | | 7 | | | 46 | | | 83 | | | A | | | 3 | | |
|---|---|---|---|---|---|---|---|---|---|---|---|---|---|---|---|---|---|---|
| | \multicolumn{15}{l}{Applied amount kg/hectare} | | | |
| | 1 | ½ | ¼ | 1 | ½ | ¼ | | | | | | | 1 | ½ | ¼ | 1 | ½ | ¼ |
| wheat | 2 3 8 | | | 3 8 9 | | | 4 6 9 | | | 3 5 5 | | | 9 9 9 | | | 3 9 9 | | |
| soyabean | 8 8 9 | | | 9 9 9 | | | 9 9 9 | | | 8 9 9 | | | 9 9 9 | | | 3 9 9 | | |
| cotton | 6 7 8 | | | 9 9 9 | | | 8 9 9 | | | 8 9 9 | | | 9 9 9 | | | 3 9 9 | | |
| sugar beet | 7 8 8 | | | 9 9 9 | | | 8 9 9 | | | 8 8 9 | | | 9 9 9 | | | 3 9 9 | | |
| Avena fatua | 1 1 1 | | | 2 3 4 | | | 1 2 2 | | | 1 1 1 | | | 4 8 9 | | | 2 2 | | |
| Bromus tectorum | 4 6 7 | | | 2 2 2 | | | 1 1 1 | | | 2 4 6 | | | 9 9 9 | | | 3 8 9 | | |
| Alopecurus myos. | 1 2 2 | | | 2 3 4 | | | 2 2 2 | | | 1 1 2 | | | 3 5 8 | | | 2 2 | | |
| Digitaria sang. | 1 2 2 | | | 1 1 2 | | | 1 1 1 | | | 1 2 2 | | | 1 2 2 | | | 1 2 | | |
| Echinochloa c.g. | 1 1 1 | | | 1 1 4 | | | 1 1 1 | | | 1 1 2 | | | 1 1 2 | | | 1 1 | | |
| Sorghum halepense | 1 1 1 | | | 2 2 3 | | | 2 2 4 | | | 1 1 1 | | | 1 2 5 | | | 1 1 | | |

In these tests, the compounds according to the present invention exhibit in the control of weeds an action which is superior to that of the known compounds.

Reduction of growth of grasses

Seeds of the grasses Lolium perenne, Poa pratensis, Festuca ovina and Dactylis glomerata are sown in a soil/peat/sand mixture (6:3:1) in plastic trays and watered in the usual manner. The emerged grasses are cut back each week to a height of 4 cm, and are sprayed 40 days after sowing and 1 day after the last cutting with an aqueous spray liquor of in each case a compound of the formula I. The amount of active ingredient is equivalent to 0.05-2 kg of active ingredient per hectare. The growth of the grasses is compared, 10 and 21 days after application, with that of the untreated control specimens. The compounds Nos. 1, 7, 46 and 83 in an amount of 0.05 kg per hectare reduce the growth of the grasses by 18-32%.

We claim:

1. A compound selected from the group consisting of a chlorofluoropyridine of the formula:

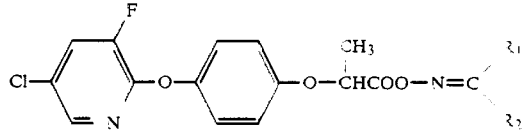

wherein each of $R_1$ and $R_2$ is alkyl of 1 to 4 carbon atoms.

2. α-[4-(3'-Fluoro-5'-chloropyridyl-2'-oxy)-phenoxy]-propionic acid acetoxime ester according to claim 1.

3. A herbicidal and plant growth regulating composition comprising an effective amount of a compound according to claim 1 and an inert carrier therefor.

4. The method of controlling weeds which comprises applying thereto or to the locus of the weeds' growth an effective amount of a compound according to claim 1.

* * * * *